United States Patent

Buysse et al.

[19]

[11] Patent Number: 5,827,271
[45] Date of Patent: Oct. 27, 1998

[54] ENERGY DELIVERY SYSTEM FOR VESSEL SEALING

[75] Inventors: Steven P. Buysse, Longmont; Jenifer S. Kennedy; S. Wade Lukianow, both of Boulder; Thomas P. Ryan, Fort Collins, all of Colo.

[73] Assignee: Valleylab, Boulder, Colo.

[21] Appl. No.: 530,495

[22] Filed: Sep. 19, 1995

[51] Int. Cl.⁶ .................................................. A61B 17/36
[52] U.S. Cl. ............................................. 606/40; 606/34
[58] Field of Search ........................ 606/32–48, 205–210

[56] References Cited

U.S. PATENT DOCUMENTS

| | | |
|---|---|---|
| 4,474,179 | 10/1984 | Koch . |
| 4,559,943 | 12/1985 | Bowers ..................................... 606/37 |
| 4,860,745 | 8/1989 | Farin et al. ............................... 606/40 |
| 5,151,102 | 9/1992 | Kamiyama et al. . |
| 5,201,900 | 4/1993 | Nardella . |
| 5,207,691 | 5/1993 | Nardella . |
| 5,423,809 | 6/1995 | Klicek ...................................... 606/38 |
| 5,423,810 | 6/1995 | Goble et al. .............................. 606/40 |
| 5,483,952 | 1/1996 | Aranyi ................................ 606/205 X |

FOREIGN PATENT DOCUMENTS

| | | |
|---|---|---|
| 0556705 | 2/1993 | European Pat. Off. . |
| WO 9206642 | 4/1992 | WIPO . |
| WO 9424949 | 11/1994 | WIPO . |
| WO 9519148 | 7/1995 | WIPO . |

OTHER PUBLICATIONS

Studies on Coagulation and the Development of an Automatic Computerized Bipolar Coagulator., J. Neurosurg., vol. 75, Jul. 1991.

Automatically Controlled Bipolar Electrocoagulation—"COA–COMP"., Neurosurg. Rev.. (1984), pp. 187–190.

*Primary Examiner*—Brian Casler
*Assistant Examiner*—Ryan Carter

[57] ABSTRACT

Electrosurgical energy is used in combination with a surgical tool to seal vessels and vascular tissue of a patient. One of the important advances of the present system is that it can effectively seal vessels of a patient without leaving any foreign material in the body of the patient. The present system is also capable of sealing vessels as large as ten millimeters in diameter. Another advantage of the present system is that the surgeon can visually inspect the integrity of the seal. The invention works with a combination of pressure and controlled application of electrosurgical energy to achieve the desired result. A surgical tool is used to grasp and apply an appropriate amount of closure force to the tissue of the patient. The tool is capable of conducting electrosurgical energy to the tissue concurrently with the application of the closure force. A method for sealing vessels and vascular tissue of a patient includes the steps of applying pressure to the vessels and other tissues of the patient; applying a first level of electrosurgical power to the vessels and other tissue sufficient to melt proteins in the tissue; applying a second level of electrosurgical power to the vessels and other tissue sufficient to cause desiccation without charring; reducing the electrosurgical power substantially to zero for a length of time sufficient to allow the vessels and other tissues to cool into a new compressed form; and relieving the pressure on the tissue.

19 Claims, 2 Drawing Sheets

ENERGY DELIVERY SYSTEM FOR VESSEL SEALING

FIELD OF THE INVENTION

This invention pertains to a medical system for sealing vessels and other vascular tissue, and more particularly to a system for applying pressure in combination with electrosurgical energy to the tissue of a patient for permanently sealing flow through the vessels and vascular tissue.

BACKGROUND OF THE DISCLOSURE

Ligation or occlusion of ducts, veins, arteries, vascular bundles, or blood vessels is common in many surgical procedures. Larger structures are typically sealed by using sutures. Ligating clips are sometimes used in procedures where it is difficult or time-consuming to suture the vessel. The placement and integrity of the clip needs to be carefully checked by the surgeon. If the staple or clip were to become dislodged, the result could be undesirable bleeding. Surgeons often use several clips or staples in order to insure the integrity of the closure.

Some devices for clipping vessels include the use of electrosurgical energy to aid in securing the clip. U.S. Pat. No. 5,207,691 discloses an electrosurgical clip applicator in which electrosurgical energy is applied through the clip to the tissue. The electrosurgical energy causes the clip and the adjacent tissue to be fused together, resulting in a more secure placement.

U.S. Pat. No. 5,201,900 discloses a bipolar surgical clip having two separated conductive portions. A bipolar electrosurgical instrument can be used to apply energy to the clip. One prong of the clip is connected to the active electrode, and the other prong of the electrode is connected to the return electrode.

All of the aforementioned systems suffer from the drawback of leaving foreign material in the patient. Other methods for sealing structures have been disclosed, although none has gained wide acceptance because of reliability concerns. For example, U.S. Pat. No. 5,151,102 discloses a blood vessel coagulation/stanching device which operates with bipolar electrosurgical energy. The device operates with a pair of forceps for grasping the vessel and applying electrosurgical energy. During this process, the vessel walls shrink and the tissue becomes rigid. This method has been unreliable and inadequate for sealing structures which are larger than approximately two millimeters in diameter.

Several journal articles have disclosed methods for sealing small blood vessels using electrosurgery. An article entitled *Studies on Coagulation and the Development of an Automatic Computerized Bipolar Coagulator*, J. Neurosurg., Volume 75, July 1991, describes a bipolar coagulator which is used to seal small blood vessels. The article states that it was not possible to safely coagulate arteries with a diameter larger than 2 to 2.5 mm.

A second article is entitled *Automatically Controlled Bipolar Electrocoagulation —"COA-COMP"*, Neurosurg. Rev. (1984), pp. 187–190. This article describes a method for terminating electrosurgical power to the vessel so that charring of the vessel walls can be avoided. The electrosurgical power is terminated when the impedance of the load on the generator has reached a local minimum. This article addresses applications in neurosurgery and precision surgery where the vessel diameters are small.

A related patent application entitled "Vascular Tissue Sealing Pressure Control and Method", attorney docket number PC 9200, has been filed concurrently with this application.

SUMMARY OF THE INVENTION

One of the important advances of the present system is that it can effectively seal larger vessels of a patient without leaving any foreign material in the body of the patient. The present system is capable of sealing vessels as large as ten millimeters in diameter. Another advantage of the present system is that the surgeon can visually inspect the integrity of the seal.

This invention works with a combination of pressure and controlled application of electrosurgical energy to achieve the desired result. Therefore, the system requires a tool to grasp and apply an appropriate amount of pressure to the tissue of the patient. The term "pressure" refers to the closure force on the vessels or other tissue that is applied by the end effectors of the tool. The tool must also be capable of conducting electrosurgical energy to the tissue concurrently with the application of pressure.

An electrosurgical generator is used to generate the electrosurgical energy. The electrosurgical energy is preferably applied in a specified manner by using an automatic control system. The control system regulates the output current and the output voltage of the electrosurgical generator in a manner that provides optimal vessel sealing.

One of the advances of the present invention is that a high current is applied to the tissue in order to melt the proteins. The high current is important for its effect on the tissue. Similarly, the output voltage is regulated to reduce sparking and localized tissue heating. The voltage is preferably kept below one hundred sixty volts RMS, and in the preferred embodiment is kept below one hundred twenty volts RMS.

Earlier attempts to seal vessels with electrosurgery were unsuccessful in part because a relatively low current was applied. The present invention may draw a maximum current in excess of two amperes RMS through the tissue. This level of output current is higher than the design capabilities of many presently available electrosurgical generators.

Charring of the tissue can be avoided by terminating the flow of electrosurgical energy to the tissue at an appropriate time. There are several techniques for determining when to terminate the electrosurgical energy. One technique is to monitor the impedance of the output load on the electrosurgical generator. When the impedance reaches a certain level, preferably above one thousand ohms, the electrosurgical energy should be terminated.

Another technique is to monitor the phase angle between the output voltage and the output current. Energy delivery to the surgical tool should be terminated preferably when the output current leads the output voltage by an angle greater than approximately fifty degrees.

A third technique for determining when to terminate the electrosurgical energy is to monitor the output current. As the tissue desiccates, the amount of electrical current flowing through the tissue decreases. The generator may terminate the energy delivery to the surgical tool when the output current drops below approximately 200 milliamperes RMS.

It is preferable to maintain pressure on the vessels or tissue of the patient for a short time after the electrosurgical energy has been substantially terminated. This allows the tissue to cool in its newly sealed state. An audible tone indicator in the generator is preferably available to indicate to the surgeon when it is appropriate to release the pressure on the tissue. The time delay may be up to five seconds after terminating the energy delivery to the surgical tool.

In the preferred embodiment there are four main steps for using the tissue sealing system. The first step may include applying and maintaining pressure on the tissue. The second step may include rapidly heating the tissue with electrosurgical energy. The third step may include lowering the energy which is delivered to the tissue so that the tissue will desiccate without charring. The final step may include terminating the electrosurgical energy delivery to the tissue so that the tissue is allowed to cool while still under pressure.

An automatic control system is preferably located within the electrosurgical generator and has, as one of its functions, the ability to automatically transition through the different levels of electrosurgical energy delivery. In an alternative embodiment, the power delivery to the surgical tool may not have discrete, step-wise levels. Instead, the power delivery may be a smooth function which initially delivers a high current, and then transitions to a lower power lever to desiccate the tissue, followed by termination of the power delivery when the impedance of the tissue rises above approximately one thousand ohms.

What follows is a summary of the various embodiments of the invention. The preferred embodiment of the electrosurgical energy delivery system is used for sealing vessels and other tissues of a patient. The system comprises a generator, a surgical tool, and means for controlling the level of electrosurgical energy which is delivered to the tissue.

The generator is preferably capable of delivering a controlled level of high frequency electrosurgical energy. The output of the generator may be characterized as having an output voltage and an output current which are each regulated in the preferred embodiment. The generator in the present system could limit the output voltage to a value below one hundred sixty volts RMS, and most preferrably would be limited below one hundred twenty volts RMS. One of the reasons for limiting the output voltage is to avoid sparks and arcing which cause local high temperature zones in the tissue, and can also result in the tissue sticking to the electrodes. Another disadvantage of arcing is that it may result in transection of the vessel.

The surgical tool is most preferably connected to the generator output for receiving the electrosurgical energy. The surgical tool may take the form of forceps, clamps, or any instrument with articulating members for grasping tissue.

In a bipolar configuration, one member of the surgical tool will be electrically connected to be an active electrode, and another member of the surgical tool will be electrically connected to be a return electrode. Alternatively, in a monopolar arrangement, the surgical tool may be electrically connected to only one electrical pole of the generator, while the patient is electrically connected to the other electrical pole. While the members are grasping tissue, electrosurgical energy from the generator will flow in circuit through the tissue.

In the preferred embodiment, there are means for controlling the level of electrosurgical energy delivered to the surgical tool. The level of electrosurgical energy is controlled such that the vessels and other tissues are sealed as they are grasped by the members of the surgical tool. The level of electrosurgical power may refer to the RMS power output of the generator, which may be a function of output voltage, output current, frequency, and duty cycle.

The surgical tool may also have means for applying pressure to the vessels and other tissues between the members concurrently with the application of the electrosurgical energy. The pressure application means can take of the form of a latch or indent which holds a known spring force against the members of the tool. There may be several selectable levels of pressure available from the surgical tool. For example, it may be desirable to apply a high level of pressure to arteries and vascular tissue, and a lower level of pressure to veins.

During an operation, the surgeon may grasp a vessel with the surgical tool and operate the mechanisms on the tool to apply the desired level of pressure to the vessel. Once the pressure has been applied to the vessel, the surgeon may activate the electrosurgical energy. The generator applies the appropriate amount of electrosurgical energy according to a specified power curve.

There are several methods for feedback control to the generator. Feedback control is important because the transition points in the power curve are scheduled to occur according to the state of the tissue. In addition, it would be undesirable to apply too much energy to the tissue and thus cause charring and sticking. Several parameters may be monitored for purposes of feedback control. These parameters include the impedance of the tissue, the phase angle between the output voltage and output current, the level of output current flowing through the tissue, and the temperature of the tissue.

It is preferable for the generator to have means for at least approximating impedance of the vessels and other tissues of the patient as they are grasped by the members of the surgical tool. For example, one way to approximate the impedance of the tissue is to assume that the impedance is mostly resistive, and thus make the approximation by dividing the output voltage by the output current. Other numerical techniques for approximating impedance are available so that a long division need not be performed. One such approximation technique is to scale the output voltage and output current appropriately so that a range of impedance may be estimated by mere comparison and bit shifting in a digital circuit.

Impedance of the tissue is a good indicator of the state of desiccation of the tissue. One reason for having an estimate of the impedance is to control the level of electrosurgical energy so that it is substantially terminated when the impedance of the vessels and other tissues rises above approximately one thousand ohms. In certain embodiments of the invention, it may be convenient to terminate the energy delivery to the surgical tool when the estimate of impedance rises above 2048 ohms.

The preferred means for controlling the level of electrosurgical energy comprises several stages. The first stage is a rapid power delivery function for rapidly increasing the power delivery to the vessels and other tissues until a first impedance breakpoint is reached. The second stage is a constant power delivery function for maintaining a constant power delivery to the vessels and other tissues until proteins in the vessels and other tissues have melted. The third stage is a low power delivery function for maintaining a low power delivery to the vessels and other tissues until a second impedance breakpoint is reached. In the preferred embodiment, the transitions between the stages are executed automatically in the generator without further input from the surgeon. The impedance breakpoints are preferably 16 ohms for the first breakpoint, and 2048 ohms for the second breakpoint.

A method for sealing vessels and other tissues of a patient is also claimed. The method comprises the steps of: applying pressure to the vessels and other tissues of the patient; applying a first level of electrosurgical energy to the vessels and other tissue sufficient to melt proteins in the tissue; applying a second level of electrosurgical energy to the vessels and other tissue sufficient to cause desiccation without charring; reducing the electrosurgical energy substantially for a length of time sufficient to allow the vessels and other tissues to cool into a new compressed form; and relieving the pressure on the tissue. The step of relieving the pressure on the tissue may occur after a delay of less than five seconds. Additionally, there may be a step of creating an audible indication after the delay is over.

An additional step in the method may be approximating impedance of the vessels and other tissues. If this step is carried out, there may be another step of terminating the second level of electrosurgical energy after the impedance of the vessels and other tissues rises above approximately one thousand ohms.

DETAILED DESCRIPTION OF THE INVENTION

Figure 1:
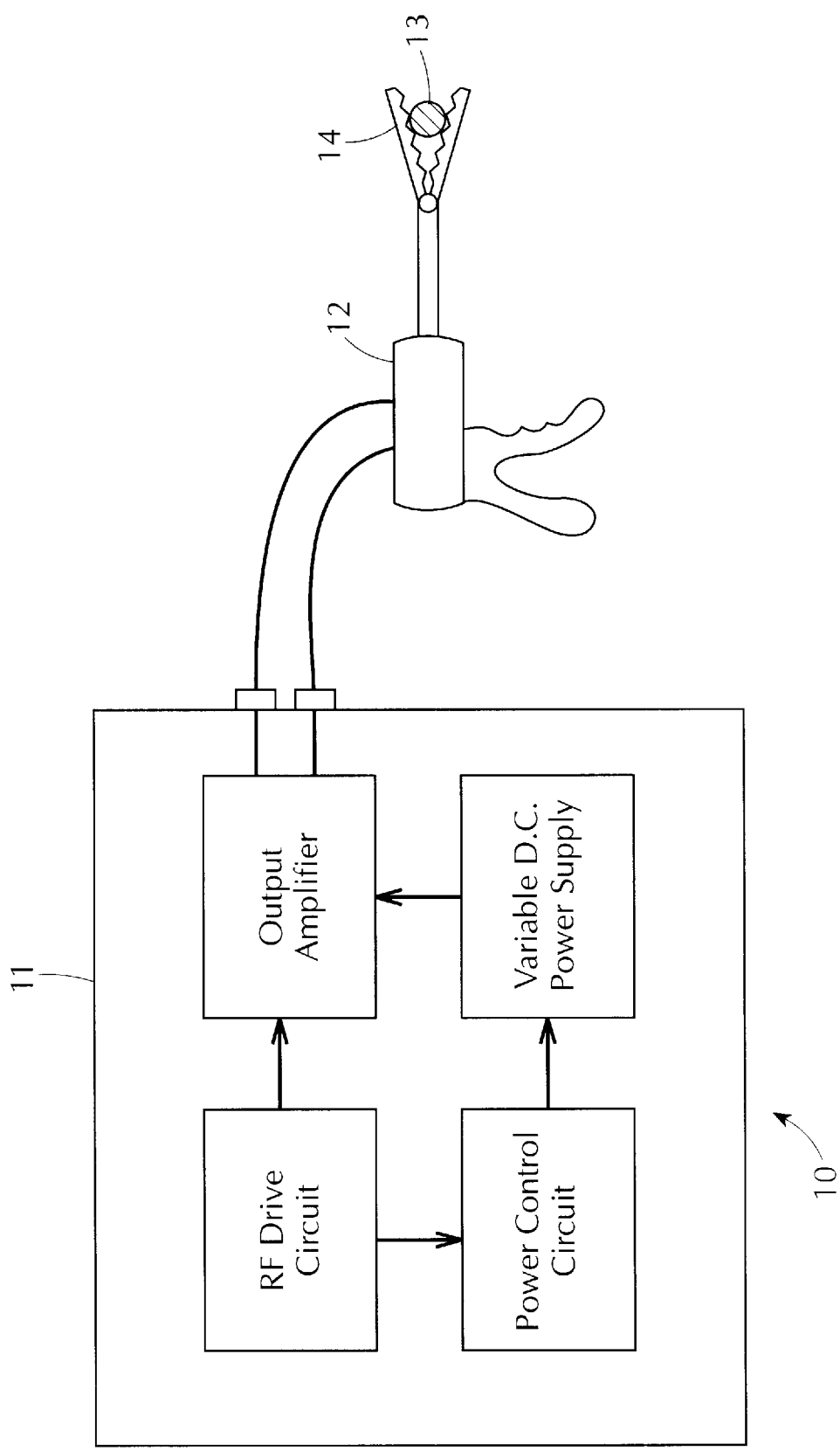
FIG. 1 is a schematic diagram of an electrosurgical vessel sealing system.

An electrosurgical energy delivery system 10 is shown in FIG. 1. The system 10 is used for sealing vessels and other tissues of a patient 13, including ducts, veins, arteries, and vascular tissue. The system 10 comprises an electrosurgical generator 11, a surgical tool 12, and means to control the output of the electrosurgical generator 11 such that it works cooperatively with the surgical tool 12 to effectively seal vessels and other tissues of a patient 13.

The electrosurgical generator 11 must be capable of delivering a controlled level of electrosurgical output power. The output power may be controlled by adjusting the output current and the output voltage. The surgical tool 12 is electrically connected to the generator 11 for receiving the electrosurgical power. The surgical tool 12 has members 14, or end effectors, capable of grasping the vessels and other tissues of the patient 13. The members 14 are also capable of applying and maintaining a relatively constant level of pressure to the vessel.

The electrosurgical generator 11 must have means for automatically controlling the level of electrosurgical power delivered to the surgical tool 12. This can be in the form of a feedback control system. In the preferred embodiment, there are also circuits for limiting the output current and the output voltage. In one embodiment, an adjustable high voltage power supply is used to adjust an RF output stage for controlling the electrosurgical output.

Figure 2:
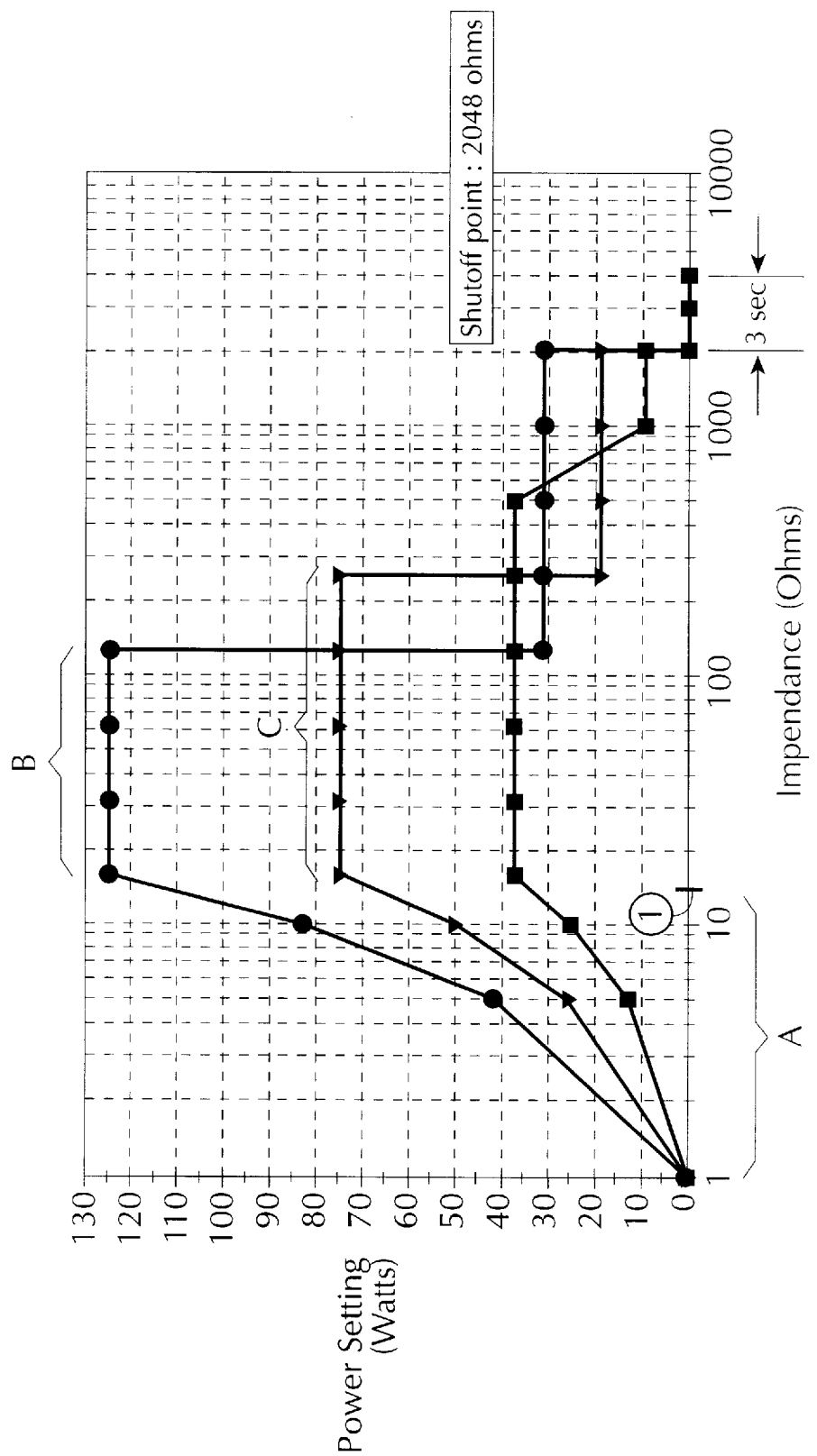
FIG. 2 is a set of power curves which represent the electrosurgical power delivered to the tissue as a function of the tissue impedance.

The power output of the generator 11 is described in terms of a power curve, and a preferred embodiment is shown in FIG. 2. The power curve may be described in terms of several stages. The stages may be discrete, or may be approximated by a smooth continuous function. In the first stage of the power curve, the electrosurgical generator 11 delivers output power even at impedances below approximately sixteen ohms, and holds a high power lever until the proteins in the tissue have sufficiently melted. During this first stage, the output current is allowed to increase to a maximum amplitude which is typically greater than two amperes RMS. It has been found that a high current is important for effective vessel sealing.

After the first stage, the electrosurgical power is lowered to a level sufficient to desiccate the vessels and other tissues. The lower power enables the desiccation to occur without charring the tissue.

A final stage involves allowing the tissue to cool into its new sealed form. During this final stage, the application of electrosurgical power to the tissue is substantially terminated. After the tissue has cooled, the closure force is released. The length of time for cooling is typically less than five seconds. In the preferred embodiment, a audible tone would indicate to the surgeon that the sealing process was complete. The surgeon would thereafter release the vessel from the surgical tool 12.

It is thought that the initial high current causes proteins in the tissue to melt. The subsequent lower power delivery to the tissue allows the proteins to cross link. As the tissue cools, the new cross linked tissue will form a permanent seal of the vessel.

The surgical tool 12 may further comprise an index for selectively applying multiple levels of closure force between the members 14. For example, arteries will require a greater closure force than veins. It has been found that a closure force of greater than 1500 grams is effective for sealing arteries. A closure force of less than 500 grams is effective for sealing veins.

In the preferred embodiment, the surgical tool 12 will have a spring that compresses to hold a closure force on the members 14. The index is mechanically linked to the spring such that each successive stop on the index holds a higher compression on the spring. The spring will not begin to compress until the members 14 encounter resistance to closure.

In the preferred embodiment, the generator 11 further comprises means for approximating impedance of the vessels and other tissues of the patient 13 as they are grasped by the members 14 of the surgical tool 12. The calculation of impedance can require long division and other lengthy mathematical manipulations. There are a variety of techniques for making a quick approximation of impedance which would be sufficient for purposes of controlling the power output of the electrosurgical generator 11. For example, comparison of the output voltage with the output current can yield an estimate of the impedance without resorting to long division.

The impedance of the tissue gives an indication of the state of desiccation of the tissue. By monitoring impedance, the generator 11 can provide the appropriate amount of electrosurgical energy without charring the tissue. For example, the power control circuit includes a power cutoff function for substantially terminating the power delivery to the surgical tool 12 when the impedance of the vessels and other tissues rises above approximately one thousand ohms.

The power control curves shown in FIG. 2 represent the electrosurgical output of the generator 11 as a function of tissue impedance. At low impedances, the electrosurgical power is increased by rapidly increasing the output current, as shown by the segment labeled A. The increase in electrosurgical power is terminated after a first impedance breakpoint is reached. The first impedance breakpoint is shown as Point 1 in FIG. 2. In the preferred embodiment, this point is typically below 20 ohms.

Next, the electrosurgical power is held approximately constant until proteins in the vessels and other tissues have melted. The impedance at which this segment ends will vary in accordance with the magnitude of the RMS power. Thus, where the maximum RMS power is approximately 125 Watts, this segment will end at approximately 128 ohms. This is shown as the segment labeled B in FIG. 2. Where a lower power is used, such as 75 Watts, the segment may end at 256 ohms. This is shown as the segment labeled C in FIG. 2.

Next, the output power is lowered to less than half of its maximum value. The low power delivery is terminated when a second impedance breakpoint is reached. In the preferred embodiment, the second breakpoint is approximately at 2048 ohms.

As an alternative to using impedance to determine the second breakpoint, the phase angle between current and voltage may be used. In this alternative embodiment, the generator 11 includes means for substantially terminating the power delivery to the surgical tool 12 when the output current leads the output voltage by an angle greater than approximately fifty degrees.

In yet another alternative embodiment, the generator 11 will terminate the power delivery to the surgical tool 12 when the output current drops below approximately 200 milliamperes RMS.

It is desirable to have the generator 11 limit its output voltage at all times to less than one hundred sixty volts RMS. The reason for keeping the output voltage low is to prevent arcing and the resulting localized tissue burn spots which might cause the tissue seal to fail.

A method for sealing vessels and other tissues of a patient 13 comprises the following steps. First, apply a closure force to the vessels and other tissues of the patient 13 sufficient to substantially close off the interior passages of the vessels or tissue. Second, apply a first level of electrosurgical power to the vessels and other tissues, wherein the peak output current is greater than two amperes and the peak output voltage is less than one hundred sixty volts RMS. Third, reduce the electrosurgical power to a second level which is less than half of the first level. Fourth, apply the second level of electrosurgical power to the vessels and other tissue of the patient 13 for a length of time sufficient to cause desiccation without charring. Fifth, reduce the electrosurgical power substantially for a length of time sufficient to allow the vessels and other tissues to cool into a new compressed form. Sixth, relieve the closure force on the tissue.

The fifth step of reducing the electrosurgical power can be accomplished either by terminating the power to the surgical tool 12, or by reducing the power to the surgical tool 12 to a very low level. In one embodiment, the electrosurgical energy would be terminated completely so that the tissue 13 would cool in the fastest time possible. In an alternative embodiment, the generator 11 would continue to output approximately one watt of power for the purpose of maintaining a closed circuit with the tissue 13 until the tissue has cooled into its compressed form.

In the preferred embodiment, the method for sealing vessels and other tissues will have the additional step of periodically approximating the impedance of the vessels and other tissues. This step will enable a control system in the generator 11 to adjust the output power in accordance with the impedance of the tissue. For example, the step of applying a second level of electrosurgical power would be terminated after the impedance of the vessels and other tissues rises above approximately one thousand ohms.

Alternatively, the step of substantially terminating the power delivery to the surgical tool 12 can occur when the output current leads the output voltage by an angle greater than approximately fifty degrees. An additional alternative is to terminate the power delivery to the surgical tool 12 when the output current drops below approximately 200 milliamperes RMS.

In the preferred embodiment, there are additional steps of limiting the output voltage to a value below approximately one hundred sixty volts RMS, and audibly indicating when the closure force on the vessels and other tissues should be removed. The audible indication occurs after substantially reducing the level of electrosurgical power, and after a further delay of less than five seconds.

It is to be understood that the above described arrangements are only illustrative of the application of the principles of the present invention. Numerous modifications and alternative arrangements may be devised by those skilled in the art without departing from the spirit and scope of the present invention. The appended claims are intended to cover such modifications and arrangements.

What is claimed is:

1. An electrosurgical energy delivery system for sealing interior passageways of vessels of a patient, the system comprising:

a generator capable of delivering electrosurgical power by producing an output voltage and an output current, the generator having means for substantially terminating the power delivery to the surgical tool when the output current drops below approximately 200 milliamperes RMS;

a surgical tool electrically connected to the generator for receiving the electrosurgical power, the surgical tool having electrically conductive members arranged for grasping the vessels of the patient and for transmitting the electrosurgical power thereto, the surgical tool having means for maintaining a closure force between the members sufficient to substantially close the interior passageways, and a power control circuit in the generator for automatically sequencing the electrosurgical power delivered to the surgical tool while the output voltage is kept below one-hundred-sixty volts RMS, wherein the sequence includes raising the output current to a maximum amplitude greater than about two amperes RMS while the surgical tool is applying the closure force, thereafter lowering the electrosurgical power to desiccate the vessels without charring, and hereafter terminating the electrosurgical power to the surgical tool.

2. The electrosurgical energy delivery system of claim 1 wherein the means for maintaining the closure force in the surgical tool further comprises means for selectively applying multiple levels of closure force between the members.

3. The electrosurgical energy delivery system of claim 1 wherein the generator further comprises means for approximating impedance of the vessels and other tissues of the patient as they are grasped by the members of the surgical tool.

4. The electrosurgical energy delivery system of claim 3 wherein the power control circuit includes a power cutoff function for substantially terminating the power delivery to the surgical tool when the impedance of the vessels and other tissues rises above approximately one thousand ohms.

5. The electrosurgical energy delivery system of claim 3 wherein the power control circuit further comprises:

an output current delivery capability for rapidly increasing the output current delivery to the vessels and other tissues until a first impedance breakpoint is reached;

a constant power delivery capability for maintaining a constant power delivery to the vessels and other tissues until proteins in the vessels and other tissues have melted; and a low power delivery capability for maintaining a low power delivery to the vessels and other tissues until a second impedance breakpoint is reached.

6. The electrosurgical energy delivery system of claim 5 wherein the first impedance breakpoint is located at approximately 16 ohms.

7. The electrosurgical energy delivery system of claim 5 wherein the second impedance breakpoint is located at approximately 2048 ohms.

8. An electrosurgical energy delivery system for sealing interior passageways of vessels of a patient, the system comprising:

a generator capable of delivering electrosurgical power by producing an output voltage and an output current;

a surgical tool electrically connected to the generator for receiving the electrosurgical power, the surgical tool having electrically conductive members arranged for grasping the vessels of the patient and for transmitting the electrosurgical power thereto, the surgical tool having means for maintaining a closure force between the members sufficient to substantially close the interior passageways, and a power control circuit in the generator for automatically sequencing the electrosurgical power delivered to the surgical tool while the output voltage is kept below one-hundred-sixty volts RMS, wherein the sequence includes raising the output current to a maximum amplitude greater than about two amperes RMS while the surgical tool is applying the closure force, thereafter lowering the electrosurgical power to desiccate the vessels without charring, and thereafter terminating the electrosurgical power to the surgical tool;

wherein the generator includes means for substantially terminating the power delivery to the surgical tool when the output current leads the output voltage by an angle greater than approximately fifty degrees.

9. The electrosurgical energy delivery system of claim 1 wherein the generator further comprises means for substantially terminating the power delivery to the surgical tool, and an audible tone indicator for producing an audible tone after substantially terminating the power delivery to the surgical tool and after a further delay of less than five seconds.

10. A method for sealing interior passageways of vessels of a patient using electrosurgical power, the electrosurgical power having an output voltage and an output current which are applied through end effectors of a surgical tool, the method comprising the steps of:

applying compression to the vessels of the patient with the end effectors sufficient to substantially close the interior passageways;

applying a first level of electrosurgical power to the vessels, wherein the output current has a maximum RMS amplitude greater than two amperes and the output voltage is less than one hundred sixty volts RMS;

reducing the electrosurgical power to a second level which is less than half of the first level;

applying the second level of electrosurgical power to the vessels and other tissue of the patient for a length of time sufficient to cause desiccation without charring;

reducing the electrosurgical power substantially to zero for a length of time sufficient to allow the vessels to cool into a new compressed form; and relieving the compression on the vessels.

11. The method for sealing vessels and other tissues in claim 10 wherein the step of reducing the electrosurgical power substantially to zero occurs for a duration of less than five seconds.

12. The method for sealing vessels and other tissues in claim 10 further comprising the steps of:

approximating a phase angle between the output current and the output voltage, and after the step of applying a second level of electrosurgical power, substantially terminating the power delivery to the surgical tool when the output current leads the output voltage by an angle greater than approximately fifty degrees.

13. The method for sealing vessels and other tissues in claim 10 further comprising the step of substantially terminating the power delivery to the surgical tool when the output current drops below approximately 200 milliamperes RMS.

14. The method for sealing vessels and other tissues in claim 10 further comprising the step of audibly indicating when the closure force on the vessels and other tissues should be removed, the audible indication occurring after substantially reducing the level of electrosurgical power to zero, and after a further delay of less than five seconds.

15. The method for sealing vessels and other tissues in claim 10 further comprising the step of continuously limiting the output voltage to a value below approximately one hundred sixty volts RMS.

16. The method for sealing vessels and other tissues in claim 10 comprising the additional step of approximating impedance of the vessels and other tissues.

17. The method for sealing vessels and other tissues in claim 16 wherein the step of applying a second level of electrosurgical power is terminated after the impedance of the vessels and other tissues rises above approximately one thousand ohms.

18. A method for sealing interior passageways of vessels of a patient using electrosurgical power, the electrosurgical power having an output voltage and an output current which are applied through end effectors of a surgical tool, the method comprising the steps of:

applying compression to the vessels of the patient with the end effectors sufficient to substantially close the interior passageways;

approximating impedance of the vessels;

increasing the electrosurgical power to the vessels until the output current has a maximum of greater than two amperes while the output voltage is held below one hundred sixty volts RMS;

decreasing the electrosurgical power delivery to the vessels until the impedance rises above approximately one thousand ohms;

reducing the electrosurgical power substantially to zero for a duration of less than five seconds; and relieving the compression on the vessels.

19. A method for sealing interior passageways of vessels larger than 2.5 millimeters in diameter of a patient using electrosurgical power, the vessels comprised of proteins, the electrosurgical power having an output voltage and an output current which are applied through end effectors of a surgical tool, the method comprising the steps of:

applying compression to the vessels of the patient with the end effectors sufficient to substantially close the interior passageways;

increasing the electrosurgical power to the vessels until the output current has a maximum value which is sufficient to melt the proteins;

decreasing the electrosurgical power delivery to the vessels so that the vessels becomes desiccated without being charred;

reducing the electrosurgical power substantially to zero for a duration sufficient to cool the vessels into a new compressed form; and relieving the compression on the vessels.

* * * * *